United States Patent [19]

Kaetsu et al.

[11] Patent Number: 5,726,342
[45] Date of Patent: Mar. 10, 1998

[54] PROCESS FOR PRODUCING α-(TERT-ALKYL) CYANOACETIC ACID ESTER

[75] Inventors: Atsushi Kaetsu; Yoshimi Yamada, both of Osaka, Japan

[73] Assignee: Sumitomo Chemical Limited, Company, Osaka, Japan

[21] Appl. No.: 787,350

[22] Filed: Jan. 22, 1997

[30] Foreign Application Priority Data

Jan. 23, 1996 [JP] Japan .................................. 8-008944
Sep. 19, 1996 [JP] Japan .................................. 8-248042

[51] Int. Cl.$^6$ .................................................. C07C 255/35
[52] U.S. Cl. .................................................. 558/443
[58] Field of Search .................................................. 558/443

[56] References Cited

PUBLICATIONS

Liebig.Ann.Chem.718, 101–114 (1968) "Direckte ter-t.-Alkylierung CH-acider Verbindungen" von Peter Boldt.
J.Am. Chem. Soc.92, (1970), pp. 4132–4133, "Rearrangememt of Azidoquinones.VII.Thermal Cleavage of 2,5–Diazidoquinones to Cyanoketenes. Syntheses of t–Butylycyanoketene" James V. Beitz et al.
J.Am.Chem.Soc. 72 (1950) "A Synthesis of Ethyl t–Alkylcyanoacetates" Elliot R. Alexander et al. pp. 4791–4792.

*Primary Examiner*—Johann Richter
*Assistant Examiner*—Ebenezer Sackey
*Attorney, Agent, or Firm*—Cushman Darby & Cushman IP Group of Pillsbury Madison & Sutro

[57] ABSTRACT

There is provide an advantageous process for producing an α-(tert-alkyl)cyanoacetic acid ester characterized by reacting cyanoacetic acid ester with a di(lower alkyl)aluminum halide, and then reacting the resulting reaction with a tert-alkyl halide.

9 Claims, No Drawings

PROCESS FOR PRODUCING α-(TERT-ALKYL) CYANOACETIC ACID ESTER

FIELD OF INVENTION

The present invention relates to a process for producing an α-(tert-alkyl)cyanoacetic acid ester, which is useful as a production intermediate of plant disease control agents.

DESCRIPTION OF RELATED ART

It is described in Japanese Patent Kokai (Laid-Open) No. 2-76846 that N-[1-(2,4-dichlorophenyl)ethyl]-2-cyano-3,3-dimethylbutaneamide, etc. has an excellent plant disease control activity, and there has been required an advantageous process for producing an α-(tert-alkyl)cyanoacetic acid ester which is useful for producing the amide compound.

Under these circumstances, the present inventors have intensively studied about the advantageous process for producing an α-(tert-alkyl)cyanoacetic acid ester. As a result, it has been found that the α-(tert-alkyl)cyanoacetic acid ester can be readily obtained from cyanoacetic acid ester and a tert-alkyl halide using a di(lower alkyl)aluminum halid. Thus, the present invention has been completed.

SUMMARY OF INVENTION

That is, the present invention provides a process for producing an α-(tert-alkyl)cyanoacetic acid ester, which comprises the steps of:

(a) reacting a cyanoacetic acid ester with a di(lower alkyl)aluminum halide and then (b) reacting the resulting reaction product with a tert-alkyl halide.

DESCRIPTION OF PREFERRED EMBODIMENT

Hereinafter, the process of the present invention will be explained in detail. First description will be made on the first step (a) of the present process.

The cyanoacetic acid ester to be used in the present process is not specifically limited, and any ester that does not adversely affect the reaction can be used. For example, cyanoacetic acid alkyl ester, phenyl ester or benzyl ester may be used in the present process.

Examples of the alkyl group of the cyanoacetic acid alkyl ester include a $C_1$–$C_8$ alkyl group such as methyl, ethyl, i-propyl, n-propyl, n-butyl, sec-butyl, i-butyl, t-butyl, n-pentyl, i-pentyl, sec-pentyl, neo-pentyl, t-pentyl, n-hexyl, heptyl, octyl group. The cyanoacetic acid alkyl ester includes methyl cyanoacetate, ethyl cyanoacetate, propyl cyanoacetate, isopropyl cyanoacetate, butyl cyanoacetate, isobutyl cyanoacetate, tert-butyl cyanoacetate, etc.

The phenyl group of the phenyl ester or benzyl ester may be optionally substituted. The phenyl group which may be optionally substituted of the cyanoacetic acid phenyl ester or benzyl ester includes a phenyl group, a phenyl group which may be substituted with a halogen atom [e.g., a fluorine atom, chlorine atom, bromine atom, etc.], a lower alkyl group [e.g., $C_1$–$C_6$ alkyl group such as methyl group, ethyl group, isopropyl group, tert-butyl group, pentyl, or hexyl group etc.] or a trifluoromethyl group.

The di(lower alkyl) aluminum halide, for example, includes a di(lower alkyl)aluminum chloride [e.g. di($C_1$–$C_4$ alkyl)aluminum chloride such as diethylaluminum chloride, dimethylaluminum chloride, etc.] or a di(lower alkyl) aluminum bromide [e.g. di($C_1$–$C_4$ alkyl)aluminum bromide such as diethylaluminum bromide, dimethylaluminum bromide, etc.]. Diethyl aluminum halide, for example, can be purchased from Aldrich Chemical Company. The di(lower alkyl)aluminum halide can be used as it is or may be used in a solution form in an inert organic solvent, if necessary.

An amount of the di(lower alkyl)aluminum halide is normally within the range from 0.5 to 2 mol, based on 1 mol of the cyanoacetic acid ester.

In step (a) of the present process, the reaction is normally conducted in an inert organic solvent. The inert organic solvent includes a halogenated hydrocarbon solvent, a hydrocarbon solvent or a mixed solvent thereof. Examples of the halogenated hydrocarbon solvent include halogenated aromatic hydrocarbon such as monochlorobenzene or dichlorobenzene, and a halogenated alkyl hydrocarbon such as 1,2-dichloroethane, dichloromethane, etc. Examples of a hydrocarbon solvent include an aromatic hydrocarbon solvent such as toluene, xylene, etc.

The reaction temperature is normally within the range from 0° C. to 60° C.

The step (a) is normally conducted by adding the di(lower alkyl)aluminum halide to the cyanoacetic acid ester with stirring, followed by continuous stirring, alternatively conducted by adding the cyanoacetic acid ester to the di(lower alkyl)aluminum halide with stirring, followed by continuous stirring. The cyanoacetic acid ester may be used by dissolved in an inert organic solvent as described above, if necessary. The reaction is preferably conducted in an inert atmosphere such as nitrogen atmosphere.

Next description will be made on the step (b) of the present process.

The tert-alkyl halide, for example, includes a tert-alkyl chloride (e.g. $C_4$–$C_8$ tert-alkyl chloride such as tert-butyl chloride, tert-pentyl chloride, etc.) or a tert-alkyl bromide (e.g. $C_4$–$C_8$ tert-alkyl bromide such as tert-butyl bromide, tert-pentyl bromide, etc.).

In this step (b) the reaction is normally conducted in an inert organic solvent.

Examples of the inert organic solvent include those used in the step (a) of the present process. The reaction temperature is normally within the range from 0° C. to 60° C.

An amount of the tert-alkyl halide is normally within the range from 0.5 to 2 mol, based on 1 mol of the cyanoacetic acid ester.

The reaction of step (b) is normally conducted by adding the tert-alkyl halide to the reaction solution obtained in the step (a) with stirring, followed by continuous stirring, if necessary. The tert-alkyl halide may be used by dissolved in an inert organic solvent as described above. The reaction is preferably conducted in an inert atmosphere such as nitrogen atmosphere.

The α-(tert-alkyl)cyanoacetic acid ester can be isolated, for example, by treating the reaction product obtained after the completion of the reaction with an aqueous solution of an acid (e.g. aqueous ammonium chloride, aqueous dilute sulfuric acid, aqueous dilute hydrochloric acid, etc.) or water, optionally washing an organic layer with an aqueous sodium hydrogencarbonate, an aqueous sodium carbonate, an aqueous sodium hydroxide, water, etc., concentrating the organic layer and conducting a purifying operation such as distillation, etc. if necessary.

The α-(tert-alkyl)cyanoacetic acid ester obtained by the process of the present invention is useful as the production intermediate of pesticides (e.g. plant disease control agent, herbicide, etc.) and drugs. More specifically, the α-(tert-alkyl)cyanoacetic acid ester can be used to obtain N-[1-(2,4-dichlorophenyl)ethyl]-2-cyano-3,3-dimethylbutaneamide having an excellent plant disease control activity as described in Japanese Patent Kokai (Laid-Open) No. 2-76846 by the process described in the same gazette.

EXAMPLE

The following Examples further illustrate the process of the present invention in detail but are not to be construed to limit the scope thereof.

In the following Examples, the reaction was conducted with stirring in a nitrogen atmosphere and a pure reaction field from ethyl cyanoacetate was determined by gas chromatography (GC) under the following conditions.

Conditions of gas chromatography (GC):

Shimadzu GC-14A

Column: Capillary column DB-1 manufactured by J&W Scientific Co. (film thickness: 1.5 μm; 0.53 mm in diameter×20 m in length)

Column temperature: A column was maintained at 70° C. for 5 minutes, heated to 270° C. in a rate or 5° C./minute and then maintained at the same temperature for 5 minutes.

Carrier gas: He (flow rate: 5 ml/min.)

Detention: FID

Internal standard substance: Dipropyl phthalate

Example 1

To a solution prepared by dissolving ethyl cyanoacetate (11.3 g, 0.1 mol) in 50 g of monochlorobenzene was added dropwise a solution prepared by dissolving diethylaluminum chloride (12.1 g, 0.1 mol) in 18 g of monochlorobenzene at 35° C. to 45° C. over about 1 hour, followed by maintaining at the same temperature for 2 hours. To the solution was added dropwise a solution prepared by dissolving tert-butyl chloride (9.3 g, 0.1 mol) in 11 g of monochlorobenzene at the same temperature over about 0.5 hours, followed by reacting at the same temperature for 1 hour.

After the reaction solution was added dropwise to 122 g of aqueous 15% hydrochloric acid at 20° C. to 50° C. over about 1 hour, the solution was heated to 55° C. to 65° C. and maintained at the same temperature for 1 hour. After the solution was allowed to stand at the same temperature and partitioned, the aqueous layer was extracted with 57 g of monochlorobenzene. The organic layers were combined and then washed in turn with 34 g of aqueous 5% sodium hydrogencarbonate and 34 g of water. The organic layer to which an internal standard substance was added was analyzed by gas chromatography. As a result, the pure yield of ethyl α-(tert-butyl)cyanoacetate was 78%.

Example 2

To a solution prepared by dissolving diethylaluminum chloride (3.6 g, 0.03 mol) in 59 g of monochlorobenzene was added dropwise a solution prepared by dissolving ethyl cyanoacetate (3.4 g, 0.03 mol) in 30 g of monochlorobenzene at 35° to 45° C. over 0.2 hours, followed by maintaining at the same temperature for 0.5 hours. To the solution was added dropwise a solution prepared by dissolving tert-butyl chloride (2.8 g, 0.03 mol) in 30 g of monochlorobenzene at the same temperature over about 0.5 hours, followed by reacting at the same temperature for 2 hours.

After the reaction solution was added dropwise to 37 g of aqueous 15% hydrochloric acid at 20° C. to 50° C. over about 1 hour, the solution was heated to 55° C. to 65° C. and maintained at the same temperature for 1 hour. After the solution was allowed to stand at the same temperature and partitioned, the aqueous layer was extracted with 30 g of monochlorobenzene. The organic layers were combined and then washed in turn with 25 g of aqueous 5% sodium hydrogencarbonate and 30 g of water. The organic layer to which an internal standard substance was added was analyzed by gas chromatography. As a result, the pure yield of ethyl α-(tert-butyl)cyanoacetate was 83%.

Examples 3 to 7

According to the same manner as that described in Example 2 except for changing the scale of the reaction (charged amount of the reagent: cyanoacetic acid ester, di(lower alkyl)aluminum halide or tert-alkyl halide), kind of the reaction solvent, amount of the reaction solvent and/or reaction time, the reaction was conducted. The results of Examples 3 to 7 are shown in Table 1, together with those of Examples 1 and 2.

TABLE 1

| | Amount of each reagent (mol) | Reaction solvent (parts by weight)[*1] | | Reaction time[*2] (hour) | Pure yield[*3] (%) |
|---|---|---|---|---|---|
| Example 1 | 0.1 | Monochlorobenzene | (7.0) | 1 | 78 |
| Example 2 | 0.03 | Monochlorobenzene | (35.0) | 2 | 83 |
| Example 3 | 0.15 | Monochlorobenzene | (7.0) | 2 | 76 |
| Example 4 | 0.1 | 1,2-Dichlorobenzene | (7.0) | 5 | 73 |
| Example 5 | 0.2 | 1,2-Dichloroethane | (7.0) | 5 | 62 |
| Example 6 | 0.2 | Xylene | (7.0) | 5 | 67 |
| Example 7 | 0.03 | Toluene | (35.0) | 2 | 82 |

[*1]Total of amount of reaction solvent based on 1 part by weight of ethyl cyanoacetate
[*2]Reaction time after completion of dropwise addition of tert-butyl chloride
[*3]Yield from ethyl cyanoacetate

Example 8

To a solution prepared by dissolving ethyl cyanoacetate (90.5 g, 0.8 mol) in 453 g of monochlorobenzene was added dropwise diethylaluminum chloride (96.5 g, 0.8 mol) at 35° C. to 45° C. over about 3 hours, followed by maintaining at the same temperature for 5 hours. After this solution was cooled to 20° C., a solution prepared by dissolving tert-butyl chloride (74.1 g, 0.8 mol) in 91 g of monochlorobenzene at 15° C. to 25° C. over about 3 hours, followed by reacting at the same temperature for 2 hours.

After the reaction solution was added dropwise to 973 g of aqueous 15% hydrochloric acid at 15° C. to 25° C. over about 5 hours, the solution was maintained at the same temperature for 3 hours. After the solution was allowed to stand at the same temperature and partitioned, the aqueous layer was extracted with 453 g of monochlorobenzene. The organic layers were combined and then washed in turn with 272 g of water, 538 g of aqueous 5% sodium hydrogencarbonate and 272 g of water. The organic layer (1197 g) to which an internal standard substance was added was analyzed by gas chromatography. As a result, the content of ethyl α-(tert-butyl)cyanoacetate was 9.5% and it's pure yield was 84%.

Aliquot of the above organic layer (1100 g) was concentrated to obtain the residue (198.8 g). Then, 170.0 g of the residue was rectified (content of ethyl α-(tert-butyl) cyanoacetate determined by gas chromatography: 52.0%, purity: 88.4 g). As a result, 81.6 g of the desired product having a content (99.6%) determined by gas chromatography at the boiling point of 112° C./20 mmHg was obtained.

What is claimed is:

1. A process for producing an α-(tert-alkyl)cyanoacetic acid ester, which comprises the steps of:
   (a) reacting a cyanoacetic acid ester with a di(lower alkyl)aluminum halide and then
   (b) reacting the resulting reaction product with a tert-alkyl halide.

2. The process according to claim 1, wherein the di(lower alkyl)aluminum halide is a di(lower alkyl)aluminum chloride or a di(lower alkyl)aluminum bromide.

3. The process according to claim 1, wherein the di(lower alkyl)aluminum halide is diethylaluminum chloride.

4. The process according to claim 1, 2 or 3, wherein the tert-alkyl halide is a tert-alkyl chloride or a tert-alkyl bromide.

5. The process according to claim 1, 2 or 3, wherein the tert-alkyl halide is tert-butyl chloride and the α-(tert-alkyl) cyanoacetic acid ester is an α-(tert-butyl)cyanoacetic acid ester.

6. The process according to claim 1, 2, 3, 4 or 5, wherein the ester is an alkyl ester.

7. The process according to claim 1, 2, 3, 4, 5 or 6, wherein the reaction is conducted in an inert organic solvent.

8. The process according to claim 7, wherein the inert organic solvent is a halogenated hydrocarbon solvent, a hydrocarbon solvent or a mixed solvent thereof.

9. The process according to claim 7, wherein the inert organic solvent is at least one selected from the group consisting of monochlorobenzene, dichlorobenzene, 1,2-dichloroethane, dichloromethane, toluene and xylene.

* * * * *